US010024838B2

(12) United States Patent
Rhodes et al.

(10) Patent No.: US 10,024,838 B2
(45) Date of Patent: Jul. 17, 2018

(54) CHEMICAL DIGESTION METHODS OF QUANTIFICATION FOR WATER AND DEBRIS MIXTURES

(71) Applicant: ATOMIC ENERGY OF CANADA LIMITED / ÉNERGIE ATOMIQUE DU CANADA LIMITÉE, Chalk River (CA)

(72) Inventors: David Bruce Rhodes, Deep River, CA (US); Claire Emmalyn Simister, Deep River, CA (US)

(73) Assignee: ATOMIC ENERGY OF CANADA LIMITED, Chalk River (CA)

( * ) Notice: Subject to any disclaimer, the term of this patent is extended or adjusted under 35 U.S.C. 154(b) by 0 days.

(21) Appl. No.: 15/320,440

(22) PCT Filed: Jun. 18, 2015

(86) PCT No.: PCT/CA2015/050562
§ 371 (c)(1),
(2) Date: Dec. 20, 2016

(87) PCT Pub. No.: WO2015/192243
PCT Pub. Date: Dec. 23, 2015

(65) Prior Publication Data
US 2017/0227517 A1 Aug. 10, 2017

Related U.S. Application Data

(60) Provisional application No. 62/015,173, filed on Jun. 20, 2014.

(51) Int. Cl.
| | | |
|---|---|---|
| *G01N 1/40* | (2006.01) | |
| *G01N 31/00* | (2006.01) | |
| *G01N 33/18* | (2006.01) | |
| *G01N 33/34* | (2006.01) | |
| *G01N 5/04* | (2006.01) | |
| *H01J 49/10* | (2006.01) | |

(52) U.S. Cl.
CPC ......... *G01N 33/343* (2013.01); *G01N 1/4022* (2013.01); *G01N 1/4044* (2013.01); *G01N 5/04* (2013.01); *G01N 31/00* (2013.01); *G01N 33/18* (2013.01); *G01N 2001/4027* (2013.01); *H01J 49/105* (2013.01); *Y10T 436/25125* (2015.01); *Y10T 436/25375* (2015.01)

(58) Field of Classification Search
CPC ...... G01N 5/04; G01N 1/4005; G01N 1/4022; G01N 1/4044; G01N 2001/4027; G01N 31/00; G01N 33/18; G01N 33/343; G01N 15/00; H01J 49/105; G21C 15/00; Y10T 436/25; Y10T 436/25125; Y10T 436/25375
USPC ......... 436/2, 72, 73, 79, 147, 171, 155, 174, 436/175, 177; 422/82.05, 527, 534, 535
See application file for complete search history.

(56) References Cited

U.S. PATENT DOCUMENTS

| | | | |
|---|---|---|---|
| 7,027,628 B1 | 4/2006 | Gagnon et al. | |
| 7,391,028 B1 | 6/2008 | Rubenstein | |
| 8,199,997 B2 | 6/2012 | Rutenberg et al. | |
| 9,672,947 B2 * | 6/2017 | Rhodes | B01D 29/333 |
| 9,770,680 B2 * | 9/2017 | Haque | B01D 29/07 |
| 2011/0215059 A1 * | 9/2011 | Smith | B01D 35/02 210/806 |
| 2013/0208847 A1 * | 8/2013 | Prather | G21C 19/307 376/309 |
| 2017/0227473 A1 * | 8/2017 | Rhodes | G01N 21/94 |

FOREIGN PATENT DOCUMENTS

| | | |
|---|---|---|
| WO | 2013/105947 A1 | 7/2013 |
| WO | 2014/161585 A1 | 10/2014 |
| WO | 2015/192242 A1 | 12/2015 |
| WO | 2015/192243 A1 | 12/2015 |

OTHER PUBLICATIONS

Written Opinion dated Sep. 2, 2015 in respect of International Application No. PCT/CA2015/050562.
International Preliminary Report on Patentability dated Dec. 20, 2016 in respect of International Application No. PCT/CA2015/050562.
Ding et al., Characterization and Head-Loss Testing of Latent Debris from Pressurized-Water-Reactor Containment Buildings (NUREG/CR-6877), Jul. 2005, pp. 1-103, Office of Nuclear Regulatory Research, U.S. Nuclear Regulatory Commission, Washington, DC.
Harwood et al., Uncertainties in the ECC Strainer Knowledge Base—the Canadian Regulatory Perspective, Debris Impact on Emergency Coolant Recirculation, Workshop Proceedings, Feb. 2004, pp. 53-60, Albuquerque, NM.
Ding et al., Characterisation of Latent Debris from Pressurized Water Reactor Containment Buildings, Debris Impact on Emergency Coolant Recirculation, Workshop Proceedings, Feb. 2004, pp. 163-176, Albuquerque, NM.
Andreychek et al., Evaluation of Long-Term Cooling Considering Particulate, Fibrous and Chemical Debris in the Recirculating Fluid, Oct. 2011, Revision 2, Westinghouse Electric Company LLC, Cranberry Township, PA.
Pietrangelo et al., Pressurized Water Reactor Sump Performance Evaluation Methodology, Dec. 2004, Nuclear Energy Institute, Washington, DC.
Extended European Search Report dated Feb. 19, 2018 in respect of European Patent Application No. 15809269.2.
Ding et al., Characterization and Head-Loss Testing of Latent Debris from Pressurized-Water-Reactor Containment Buildings (NUREG/CR-6877), Jul. 2005, Office of Nuclear Regulatory Research, U.S. Nuclear Regulatory Commission, Washington, DC.

\* cited by examiner

*Primary Examiner* — Maureen Wallenhorst
(74) *Attorney, Agent, or Firm* — Bereskin & Parr LLP/S.E.N.C.R.L., s.r.l.

(57) ABSTRACT

With a water, particulate and fibre mixture, a method of quantifying fibre content may include providing a sample of the mixture, filtering the sample to produce a particulate and fibre mixture, burning the particulate and fibre mixture to produce a fibre sample, and dissolving the fibre sample to produce a fibre solution. The fibre solution may be analyzed to determine an elemental content of the fibre solution. The elemental content may be compared to a known elemental content to estimate the fibre content.

20 Claims, 4 Drawing Sheets

CHEMICAL DIGESTION METHODS OF QUANTIFICATION FOR WATER AND DEBRIS MIXTURES

CROSS-REFERENCE TO RELATED APPLICATIONS

This is a national stage application of International Application No. PCT/CA2015/050562 filed on Jun. 18, 2015, which claims priority to U.S. Provisional Application No. 62/015,173 filed on Jun. 20, 2014, and the entire contents of each are hereby incorporated herein by reference.

FIELD

The present disclosure relates to techniques for analyzing the fibre content of water and debris mixtures. The present disclosure also relates to nuclear power plant safety.

BACKGROUND

The following paragraphs are not an admission that anything discussed in them is prior art or part of the knowledge of persons skilled in the art.

In water cooled nuclear power plants, following a loss of coolant accident (LOCA), water and insulation debris dislodged at the break location may accumulate in the sump area. After the initial emergency water injection phase, the sump water may be re-circulated back to the reactor core as part of the emergency core cooling (ECC) system to prevent fuel melt. The debris in the sump water may be filtered by ECC strainers so that the debris will not deposit in the reactor core, which may result in flow blockages and buildup of thermal resistance layers on fuel elements, and may cause the fuel to overheat and melt. Although ECC strainers may catch almost all debris on the strainer surface, a small amount of debris may go through the strainer holes and into the reactor core.

Deposition of the debris in the reactor core is considered a safety issue, because the nuclear fuel keeps producing nuclear energy even after the reactor is safely shutdown (through radioactive decays of unstable isotopes produced in the core). For various water cooled reactors (e.g., PWRs, BWRs and CANDUs), there are either established safe limits of how much debris is allowed to bypass the strainers, or such limits are being developed. Although typical debris includes various types of particulates and fibres, the bypass limits may be set for the amount of fibre only. It is, hence, a functional requirement that ECC strainers be able to filter fibres so that these fibre bypass limits are not exceeded.

There are existing methods to quantify fibre bypass. These methods include collecting water samples at various times downstream of the strainer. The samples may be useful to quantify the transient evolution of the downstream fibre concentration. The samples may be processed by filtering the debris using a fine filter paper, drying the filter paper, and weighing the increase in the weight of filter paper (this technique may be referred to as the "weighing technique"). The overall fibre bypass may then be obtained by integrating the weights of the fibres obtained from individual samples over time. Alternatively, a very fine downstream filter may be used to capture all fibres that bypassed the strainer surface (this technique may be referred to as the "downstream filter technique"). This technique may be more accurate as it gives the total weight of the captured fibres, but may get plugged in some tests that use particulates.

In an actual ECC system, the short-term, high-fibre-concentration flow may last a few hours (corresponding to a few flow turnovers). The requirement for the allowable overall fibre bypass may be defined for one month of ECC operation after the start of the ECC recirculation system. The movement of individual fibres from the debris bed and occasional local collapse of the debris bed may provide a steady supply of a small amount of fibre to the downstream. Hence, even if the downstream fibre concentrations are small, a significant amount of fibre may bypass the strainers after the initial high-fibre-concentration transient. The weighing technique may be a good way of quantifying debris bypass shortly after the ECC recirculation pumps are engaged and a significant amount of debris may be bypassing the clean strainer surface. Most of this debris may end up accumulating on the strainer surface, creating a mat of fibres that may eventually behave like a layer of fine filter on top of the strainer surface. As a result, the fibre concentration downstream of the strainer may eventually become sufficiently small to render the weighing technique impractical (because the weight of the captured fibre becomes a very small fraction of the combined weight of the filter and fibre after filtering).

Hence, other techniques, suitable to quantify a small amount of fibre in water mixed with particulates, are desirable.

INTRODUCTION

The following is intended to introduce the reader to the detailed description that follows and not to define or limit the claimed subject matter.

In an aspect of the present disclosure, a method of quantifying fibre content of a water, particulate and fibre mixture may include: providing a sample of the water, particulate and fibre mixture; filtering the sample of the water, particulate and fibre mixture to produce a particulate and fibre mixture; burning the particulate and fibre mixture to produce a fibre sample; dissolving the fibre sample to produce a fibre solution; analyzing the fibre solution to determine an elemental content of the fibre solution; and comparing the elemental content to a known elemental content to estimate the fibre content.

The step of filtering may include filtering the sample of the water, particulate and fibre mixture with an ashless filter. The step of burning may include thermally decomposing the particulate of the particulate and fibre mixture. The step of burning may include ashing of the particulate and fibre mixture in an alumina crucible. The step of dissolving may include digesting the fibre sample with hydrofluoric acid.

The step of analyzing may include using Inductively Coupled Plasma—Atomic Emission Spectrometry (ICP-AES) analysis. The elemental content may include at least one elemental composition for B, Ca, Mg, Na and Si. The elemental content may include the elemental compositions for Na and Si.

The step of comparing may include determining a fibre weight of the fibre solution. The step of comparing may include determining a weight for each element of the elemental content of the fibre solution, and the fibre weight is determined based on the weight for each element.

Other aspects and features of the teachings disclosed herein will become apparent, to those ordinarily skilled in the art, upon review of the following description of the specific examples of the present disclosure.

BRIEF DESCRIPTION OF THE DRAWINGS

The drawings included herewith are for illustrating various examples of apparatuses and methods of the present disclosure and are not intended to limit the scope of what is taught in any way. In the drawings.

DETAILED DESCRIPTION

Figure 1:
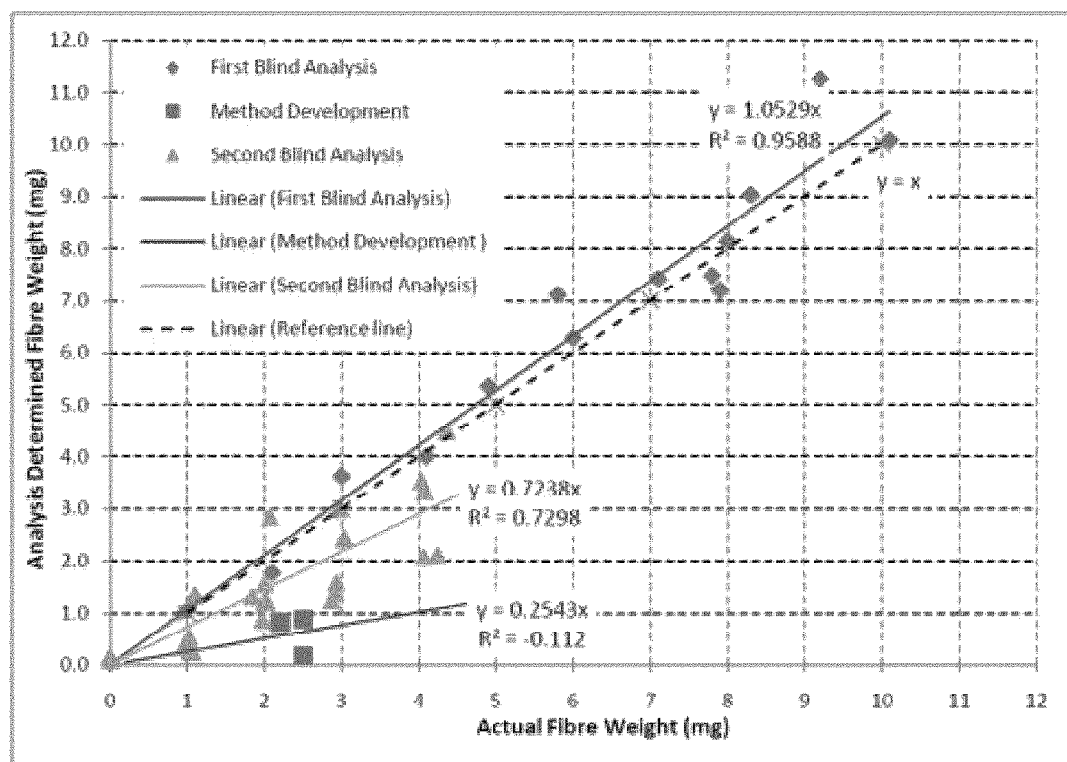
FIG. 1 is a graph showing analysis determined fibre weight versus actual fibre weight.

Various apparatuses or methods will be described below to provide an example of an embodiment of each claimed invention. No embodiment described below limits any claimed invention and any claimed invention may cover apparatuses and methods that differ from those described below. The claimed inventions are not limited to apparatuses and methods having all of the features of any one apparatus or method described below, or to features common to multiple or all of the apparatuses or methods described below. It is possible that an apparatus or method described below is not an embodiment of any claimed invention. Any invention disclosed in an apparatus or method described below that is not claimed in this document may be the subject matter of another protective instrument, for example, a continuing patent application, and the applicant(s), inventor(s) and/or owner(s) do not intend to abandon, disclaim or dedicate to the public any such invention by its disclosure in this document.

1. Chemical Digestion Technique

A sample preparation method was developed to prepare strainer insulation samples consisting of 5 to 20 mg of strainer insulation (aged NUKON and aged Telisol) and walnut shell in approximately 500 mL water (Appendix A).

In this case, walnut shell powder is used as a burnable surrogate material for particulates. Walnut shell is accepted by the United States Nuclear Regulatory Commission as an acceptable surrogate for dust, cement particles and paint chips.

It was demonstrated that the elemental compositions of the insulations and walnut shell may be successfully determined by Inductively Coupled Plasma—Atomic Emission Spectrometry (ICP-AES), even at low concentrations (5 mg in 500 mL RO water). Obtaining a representative aliquot from the strainer insulation samples was not possible, due to the in-homogeneity of the samples (the insulation fibres tended to visually clump together).

It was determined that the insulation fibres and walnut shell could be successfully isolated by filtration using ashless filters. The interference of the filter paper was then removed by ashing the sample. The ashed sample was then digested and analyzed by ICP-AES. This technique was successful in analyzing the concentration of the insulation present in samples containing as low as 5 mg of insulation in the 500 mL water sample. Percent recoveries for each element of each sample were all above 84%.

2. Fibre Weight Determined by Chemical Digestion Method

While it is conservative to perform a fibre-only bypass test for a nuclear power plant with a large amount of postulated fibrous debris, the test could prove too conservative for a nuclear plant with only a small amount of latent fibre. In the latter case, a more prototypical debris mixture (fibre and particulate) should be used in the bypass test. As noted herein, a chemical digestion method using ICP-AES analysis may provide a means to determine the weight of fibre in a bypass sample containing both fibre and walnut shell flour (the latter is currently used in strainer tests to simulate particulate debris). Two different types of fibres, Nukon and Telisol, were used in the tests. Fibre material elemental compositions are provided in Appendix B. The results are summarized in Table 1.

TABLE 1

Fibre Material Elemental Composition

| Material | Al Wt % | B Wt % | Ca Wt % | Mg Wt % | Na Wt % | Si Wt % |
|---|---|---|---|---|---|---|
| Nukon | 1.5 ± 0.2 | 1.5 ± 0.2 | 5.4 ± 0.5 | 1.7 ± 0.2 | 11 ± 1 | 25 ± 3 |
| Telisol | 0.85 ± 0.09 | 1.9 ± 0.2 | 5.1 ± 0.5 | 1.6 ± 0.2 | 11 ± 1 | 26 ± 3 |

A blind test was conducted to confirm the capabilities and limits of the chemical digestion method (Appendix B). Fifteen filtered samples were prepared. The amount of fibre and walnut shell flour in each sample was unknown. The samples were prepared and analyzed as described in Appendix B. The analysis results were tabulated for each sample in terms of elemental concentration (mg/L) for elements of Al, B, Ca, Mg, Na and Si. The results were then interpreted for the determination of the amount of fibre in each sample. The interpretation method is described as follows:

A. Determine weight of each element. The weight of each element equals its concentration (Table 6, Appendix B) times sample volume (10 mL).

B. Determine fibre weight. Fibre weight equals element weight (determined in Step A) divided by characteristic element weight percentage. Since both Nukon and Telisol fibres have similar element compositions for B, Ca, Mg, Na and Si, any of these elements or combinations of them may be used to estimate fibre weight. Because the percentage contributions are much higher than other elements, it is judged to be more accurate to use Na and Si to estimate the fibre weight. (Correlation factors of the analysis determined fibre weights to the actual fibre weights from the first blind test confirmed that analysis data from Na and Si were better than those of other elements.) To estimate the total fibre weight using Na content, for example, the measured weight of Na is divided by its weight fraction, which is 0.11. The same is done using the Si data and the total fibre weights thus estimated are averaged to reduce the effect of an outlier data point. The weight fraction of Si is 0.25 and 0.26 for Nukon and Telisol, respectively. For simplicity, Si weight fraction is assumed to be 0.25 keeping in mind that this assumption introduces 4% error if all fibres are Telisol.

C. It is noted that the percent contribution of Al is different for Nukon and Telisol. Hence, this may be used to evaluate the individual contributions of Nukon and Telisol to the overall fibre weight. Although this was achieved with some success, the scatter in Al content measurements made the predictions less accurate as compared to the overall fibre content.

The calculated fibre weight from chemical digestion and ICP-AES analysis are listed in Table 2. Note the quantity listed in column 2 of Table 2 for each sample is the average of fibre weights determined by elements Na and Si. Also listed in the table is the actual fibre weight in each sample. Each pair of values (actual weight, analysis weight) is plotted as a point in FIG. 1 and shown with diamond shaped markers. Results indicate good agreement between the actual and measured data with a maximum difference of about 20%.

It was determined that the method detection limit is approximately 5 mg. The analysis determined fibre amount was less than 50% of the actual values if the amount of fibreglass in a sample was less than 5 mg. These data are shown in FIG. 1 with square shaped markers. The results in Table 2 for samples #1, 4, 5 and 7 show relatively good matches between the analysis-determined weights and the actual weights, despite being below the reported detection limit. It is postulated that the different sample preparation methods may have contributed to the apparently contradicting conclusions. Additional work was performed to further refine the detection limit of this analysis method. For a quick comparison, the test data were also plotted in FIG. 1 as shown by the triangle shaped markers. As may be seen from the figure that most of the triangle shaped markers are located below the line y=x (the dashed line in FIG. 1), which means the analysis determined fibre weights are less than the actual fibre weights for samples having less than 5 mg fibre. As a cautious measure, in the fibre bypass test, grab samples larger than 500 mL may be taken if the fibre content in each 500 mL sample is expected to be less than 5 mg.

TABLE 2

Fibre Weight Determined from Analyses

| Sample # | Fibre Weight Determined from Analysis (mg) | Actual Fibre Weight (mg) | Weight Difference (mg) | Percent Error (%) |
| --- | --- | --- | --- | --- |
| 1 | 1.0 | 1 | 0 | 0 |
| 2 | 10.1 | 10.1 | 0 | 0 |
| 3 | 7.4 | 7.1 | 0.3 | 4 |
| 4 | 1.8 | 2.1 | −0.3 | 14 |
| 5 | 4.0 | 4.1 | −0.1 | 2 |
| 6 | 7.2 | 7.9 | −0.7 | 9 |
| 7 | 5.4 | 4.9 | 0.5 | 10 |
| 8 | 0.0 | 0 | 0 | 0 |
| 9 | 6.3 | 6 | 0.3 | 5 |
| 10 | 8.1 | 8 | 0.1 | 1 |
| 11 | 7.1 | 5.8 | 1.3 | 22 |
| 12 | 7.5 | 7.8 | −0.3 | 4 |
| 13* | 11.3 | 9.2 | 2.1 | 23 |
| 14 | 3.6 | 3 | 0.6 | 20 |
| 15 | 9.0 | 8.3 | 0.7 | 8 |

It should be noted that for sample 13, a brown residue was observed after chemical digestion. The brown residue might have contributed to the greater difference between the calculated and the actual fibre amount as compared to the differences of other samples.

3. The Second Batch of Chemical Digestion Analyses

A second batch of filtered samples was prepared for chemical digestion and ICP-AES analysis. The purpose of this analysis was to determine whether the technique may be applied to samples with fibre amount less than 5 mg. A total of 27 samples were prepared. The type of fibre and its mass in each sample were unknown. Each sample, either fibre on filter paper or blank filter paper, was ashed in an alumina crucible. The ashed sample was then digested by Aqua Regia (nitro-hydrochloric acid) and hydrofluoric acid. The digested sample was then diluted and analyzed by ICP-AES. An analysis report is provided for element concentration of Al, B, Ca, Mg, Na and Si for each sample. The information of the prepared samples is listed in Table 1 of Appendix C and the ICP-AES results are listed in Table 2 of Appendix C.

Based on element concentration provided in Table 1, and using the methodology summarized above, total fibre weights are calculated. The results are plotted in FIG. 1 in triangle-shaped markers. These results are consistent with the initial evaluation (Appendix B) in that the measured fibre content is typically under-predicted by 30% if the fibre content is less than 5 mg.

It may be concluded from the first and the second batches of analyses that the chemical digestion and ICP-AES technique may be used to determine the fibre amount in a water sample and preferably the fibre amount in the water sample should be larger than 5 mg. For samples having less than 5 mg fibre, a conservative prediction method has been developed in Appendix C. In this prediction, a factor of 1.5 is applied to the average fibre amount determined by elements Na and Si plus 1.0 mg, i.e., fibre amount in water sample=1.5×average analyzed amount from Na and Si+1.0 mg, to ensure that the predicted fibre mass is greater or equal to the actual fibre mass.

Fibre amount determined by Na and Si has an inherently higher reliability due to the element's rich presence in fibre material. Fibre amounts determined by other elements such as B and Ca could be as consistent as those of Na and Si. Analyses results reported in Appendix C demonstrate that by averaging the results from B, Na and Si or by using the fibre amount determined by B alone could not improve the final results, thus, fibre amounts used in FIG. 1 were all determined by averaging the results from Na and Si.

4. Conclusions

If fibre bypass tests are performed with fibres only, the fibrous debris that forms on the strainer surface may become fluffy and porous instead of a higher density compact debris bed if there were particulates. The porous fibre-only debris bed allows more fibres to bypass the strainer surface and, as a result, provides a conservative estimate of the fibre bypass. In some cases these tests provide conservative data that may be used to qualify a strainer design, however, in some other cases, they may be overly penalizing and may make it difficult or not possible to satisfy the fibre bypass requirement.

The methods disclosed herein may provide for a more realistic fibre bypass measurement by using a fibre-particulate mixture as in nuclear power plants. The methods disclosed herein may replace a conservative approach that ignored the presence of particulates in the water. The methods disclosed herein may help qualify strainer designs that otherwise may not satisfy the bypass acceptance criteria by reducing the conservatism that is a result of over-simplification (i.e. omission of particles) in the strainer testing.

While the present disclosure emphasizes fibre and particulate quantification in the context of nuclear power plant safety, techniques disclosed herein have the potential for use for a wide range of scientific and research activities (e.g., forensic applications), and may also be applicable in a wide range of industries (e.g., pulp and paper industry).

While the above description provides examples of one or more methods or apparatuses, it will be appreciated that other methods or apparatuses may be within the scope of the accompanying claims.

Appendix A

Analysis of Strainer Insulation in Water Samples by Inductively Coupled Plasma—Atomic Emission Spectrometry (ICP-AES)

1. Introduction

Strainer insulation samples were analyzed. The samples consist of 5 to 20 mg of strainer insulation (NUKON and Isover) and walnut shell in approximately 500 mL water.

To successfully analyze the samples, a sample preparation method was developed for the isolation and digestion of the insulation and walnut shell.

To develop the sample preparation method, four experiments were carried out. The first experiment was an analysis of each type of strainer insulation and walnut shell to determine the elemental compositions. The second experiment was an analysis of 5 to 20 mg of NUKON insulation in 50 mL of water to ensure an accurate analysis could be achieved at these concentrations. The third experiment evaluated the possibility of obtaining a representative sample from the 500 mL parent samples. The fourth experiment evaluated the use of a filtration of the 500 mL parent sample, to isolate the insulation and walnut shell. For all four experiments, all analyses of the elemental compositions were performed by Inductively Coupled Plasma—Atomic Emission Spectrometry (ICP-AES), on a Perkin-Elmer Optima 3300RL™.

2. Experiments

The following experiments were performed to develop the sample preparation method to analyze the strainer insulation present in the water samples.

2.1 Experiment 1: Determination of Elemental Composition

The elemental composition of each type of insulation (NUKON and Isover) and walnut shell was determined by ICP-AES. Samples were performed in duplicate to ensure reproducibility of the analysis.

To prepare the insulation samples, approximately 200 mg of each type of insulation was weighed out and placed in 50 mL centrifuge tubes. 10 mL of Aqua Regia was added to each centrifuge tube and left to sit overnight. The following day, 500 mL of hydrofluoric acid was added to each sample.

After the addition of acid, residual sample was observed. The samples were then centrifuged and the supernatant siphoned off. The residual was dissolved in 1.5 mL of hydrofluoric acid and recombined with the supernatant. The resulting solution was diluted to 50 mL with Reverse Osmosis (RO) water and analyzed by ICP-AES. It was observed that a small amount of residue remained for the NUKON sample after the hydrofluoric acid portion was combined with the supernatant and diluted to 50 mL.

For the walnut shell, 5 mL of RO water and 5 mL of concentrated nitric acid was added to approximately 50 mg of walnut shell in a 50 mL centrifuge tube. The sample was heated, allowed to cool and then centrifuged. As observed in the insulation samples, a residue remained. The supernatant was siphoned off and 200 mL of hydrofluoric acid was added to dissolve the residue. The hydrofluoric acid portion was recombined with the supernatant and the resulting solution was diluted to 50 mL with RO water. The sample was then analyzed by ICP-AES.

The elemental composition for the insulations and walnut shell are given in Table 1. The results achieved by ICP-DES analysis was very similar for all detectable elements to an expected composition of NUKON.

TABLE 1

Elemental Composition of Insulations and Walnut Shell

| Sample | Weight Percent (%) | | | | | |
|---|---|---|---|---|---|---|
| | Al | B | Ca | Mg | Na | Si |
| NUKON Quoted* | 1.59 | 1.24 | 5.72 | 1.81 | 9.43 | 29.92 |
| NUKON Average** | 1.4 ± 0.1 | 1.5 ± 0.1 | 5.4 ± 0.4 | 1.8 ± 0.1 | 9.2 ± 0.6 | 24 ± 1 |
| Isover Average** | 0.6 ± 0.1 | 1.8 ± 0.1 | 5.0 ± 0.4 | 1.8 ± 0.1 | 11.1 ± 0.8 | 28 ± 2 |
| Walnut Shell | <DL*** | <DL*** | 0.15 | 0.02 | 0.01 | <DL*** |

*Expected Composition
**An average of two samples
***DL = Detection Limit 2.2 Experiment 2: Analysis of Low Concentrations As the parent samples consist of only 5 to 20 mg of insulation, an experiment was performed to ensure the correct elemental composition could be detected at low concentrations.

Six samples, in total, were prepared using the NUKON insulation fibres—two 5 mg samples, two 10 mg samples, and two 20 mg samples. Samples were performed in duplicate to ensure reproducibility of the analysis. Each sample was added to 50 mL of RO water and shaken by hand. The samples were then evaporated on a hot block at 115° C. for approximately 12 hours, to near dryness. Once evaporated, 2 mL of Aqua Regia was added to each sample. The samples were digested using a hot block at 50° C. for one hour and then at 65° C. for an additional hour. The samples were then left to cool. Once cooled, 50 mL of hydrofluoric acid was added to each sample and they were allowed to sit for a couple of hours. Samples were then diluted to 10 mL with RO water and analyzed by ICP-AES.

A summary of results is given in Table 2. Very similar results to the elemental compositions were obtained and all results were reproducible. Thus, it was shown that the ICP-AES could analyze samples containing as little as 5 mg of insulation accurately.

TABLE 2

Composition Analysis of NUKON Insulation at Low Concentrations

| NUKON Sample | Weight Percent (%) | | | | | |
|---|---|---|---|---|---|---|
| | Al | B | Ca | Mg | Na | Si |
| NUKON Avg* | 1.4 ± 0.1 | 1.5 ± 0.1 | 5.4 ± 0.4 | 1.80 ± 0.13 | 9.2 ± 0.6 | 24 ± 1 |
| 5 mg | 1.5 ± 0.2 | 1.5 ± 0.2 | 4.9 ± 0.5 | 1.42 ± 0.16 | 11.5 ± 1.3 | 24 ± 3 |
| 5 mg Rep | 1.4 ± 0.1 | 1.3 ± 0.1 | 4.5 ± 0.5 | 1.36 ± 0.14 | 10.8 ± 1.2 | 23 ± 3 |
| 10 mg | 1.6 ± 0.2 | 1.5 ± 0.2 | 5.3 ± 0.5 | 1.80 ± 0.18 | 11.6 ± 1.2 | 24 ± 3 |
| 10 mg Rep | 1.6 ± 0.2 | 1.5 ± 0.2 | 5.1 ± 0.5 | 1.60 ± 0.16 | 11.5 ± 1.2 | 24 ± 3 |
| 20 mg | 1.5 ± 0.2 | 1.5 ± 0.2 | 4.9 ± 0.5 | 1.45 ± 0.15 | 11.9 ± 1.2 | 24 ± 2 |
| 20 mg Rep | 1.6 ± 0.2 | 1.5 ± 0.2 | 5.1 ± 0.5 | 1.61 ± 0.17 | 11.7 ± 1.2 | 24 ± 3 |

*As determined in Experiment 1.

2.3 Experiment 3: Aliquot Analysis from Parent Sample

The parent samples consist of 5 to 20 mg of strainer insulation (NUKON and Isover) and walnut shell in approximately 500 mL water. It is not feasible, with respect to time, to evaporate 500 mL of water on a routine basis. Thus for this experiment it was investigated if a representative aliquot may be obtained from the parent sample.

Three mock parent samples were prepared using the NUKON insulation fibres—a 5 mg sample, a 10 mg sample and a 20 mg sample. Each sample was placed in a jar with 500 mL of RO water and shaken until dispersed. A 50 mL aliquot was then taken from each prepared sample.

The 50 mL aliquots were evaporated on a hot block at 115° C. for approximately 12 hours, to near dryness. Once evaporated, 2 mL of Aqua Regia was added to each sample. The samples were digested using a hot block at 50° C. for one hour and then at 65° C. for an additional hour. The samples were then left to cool. Once cooled 50 mL of hydrofluoric acid was added to each sample and they were allowed to sit for a couple of hours. Samples were then diluted to 10 mL with RO water and analyzed by ICP-AES.

A summary of the results is given in Table 3. Very inconsistent results were obtained for both the 10 and 20 mg samples. It was also visually observed that the insulation fibres tended to clump together as oppose to uniformly disperse throughout the sample.

TABLE 3

Composition Analysis of NUKON Insulation from Aliquots of Parent Samples

| NUKON Insulation ID | Weight Percent (%) | | | | | |
|---|---|---|---|---|---|---|
| | Al | B | Ca | Mg | Na | Si |
| NUKON Avg* | 1.4 ± 0.1 | 1.5 ± 0.1 | 5.4 ± 0.4 | 1.80 ± 0.13 | 9.2 ± 0.6 | 24 ± 1 |
| 5 mg | 1.4 ± 0.2 | 1.2 ± 0.2 | 5.6 ± 0.6 | 1.62 ± 0.16 | 9.8 ± 1.0 | 20 ± 3 |
| 10 mg | 2.2 ± 0.2 | 2.0 ± 0.2 | 7.7 ± 0.8 | 2.60 ± 0.30 | 15.4 ± 1.5 | 34 ± 4 |
| 20 mg | 1.0 ± 0.1 | 1.0 ± 0.1 | 3.4 ± 0.4 | 0.98 ± 0.10 | 7.9 ± 0.8 | 17 ± 2 |

*As determined in Experiment 1

2.4 Experiment 4: Isolation of Fibres by Filtration

To isolate the insulation and walnut shell from the samples, a filtering and ashing sample preparation method was tested. When samples are ashed, all cellulose-based material will thermally decompose or "ash off", including the filter and some walnut shell constituents; however, any calcium, sodium, and magnesium from the walnut shell and the major detectable constituents of the insulation will remain in the sample.

Samples were prepared, as summarized in Table 4, in 600 mL beakers. Varying weights of NUKON were used to investigate any concentration limitations and one sample of all three components was prepared to investigate any potential interferences. Samples containing 20 mg of NUKON were performed in duplicate and samples containing 5 mg NUKON were performed in triplicate to ensure reproducibility of the sample preparation method. Samples were stirred for at least 15 minutes (or until uniformly suspended throughout the solution) with a magnetic stirrer.

TABLE 4

Samples Prepared for Vacuum Filtration Testing

| | Volume of RO | Weight of Insulation (mg) | | |
|---|---|---|---|---|
| Sample ID | Water (mL) | NUKON | Isover | Walnut Shell |
| Blank (000) | 500 | 0 | 0 | 0 |
| 001-20 | 500 | 20.0 | 0 | 0 |
| 002-20 | 500 | 19.8 | 0 | 0 |
| 003-10 | 500 | 9.9 | 0 | 0 |
| 004-5 | 500 | 5.0 | 0 | 0 |
| 005-5 | 500 | 5.1 | 0 | 0 |
| 006-5 | 500 | 5.2 | 0 | 0 |
| 007-30 | 500 | 10.1 | 10.2 | 10.1 |

To filter the samples, Whatman 40™ ashless cellulose filters were cut to 47 mm in diameter to fit the vacuum filtration apparatus. Samples were filtered using a vacuum filtration set-up. Samples were first passed through the filter paper followed by RO water rinses of the 600 mL beaker to ensure a quantitative transfer of the sample. The filters were then placed in a dessicator until ready to ash.

To ash the samples, each filter paper was transferred to a platinum crucible (with lid). The blank sample (000) was placed in the oven (muffle furnace) at 500° C. for 15 minutes. The temperature was then ramped up to 800° C., and a countdown timer set for 15 minutes was started once an internal temperature of 600° C. was reached. The crucible was removed from the oven and allowed to cool in a dessicator for approximately 5 minutes. The crucible was rinsed into a centrifuge tube using RO water. Visually, the filter paper ashed off entirely and no remnants were observable. An independent sample was also ashed using this method; however the sample melted onto the crucible and it was determined that an oven temperature of 800° C. was too high to ash the insulation samples.

Sample 001-20 was ashed at 500° C. for 15 minutes, and then the temperature was ramped up to 600° C. for 20 minutes. The crucible was removed from the oven, allowed to cool in a dessicator, and transferred to a centrifuge tube. The transfer did not require the use of RO water or a spatula. Thus, 600° C. was determined to be an ideal oven temperature for ashing the insulation samples and the remaining samples were ashed for 30 minutes at 600° C. They were transferred to centrifuge tubes following using the same procedure as sample 001-20.

Ashed samples were transferred to digestions cups and 2 mL of Aqua Regia was added to each. The samples were heated to 50° C. for an hour and then to 65° C. for an additional hour. Samples were cooled overnight and then 50 mL of hydrofluoric acid was added to each. The samples were then allowed to sit overnight and diluted to 10 mL with RO water in centrifuge tubes. A further ten times dilution was performed with RO water and the samples were analyzed by ICP-AES.

The percent recoveries achieved by this sample preparation method are given in Table 5 for the NUKON only samples; Table 6 contains percent recovery for the mixed sample (007-30). All percent recoveries were greater than 84% (all values have been corrected for the blank). Based on the results obtained from this experiment, the vacuum filtration was successful in isolating the insulation and walnut shell suspended in 500 mL of RO water and ashing was successful in eliminating any interference from the filter paper for the ICP-AES analysis.

TABLE 5

Percent Recovery of NUKON Insulation Samples Prepared by Filtration and Ashing

| | Percent Recovery (%) | | | | | |
|---|---|---|---|---|---|---|
| Sample | Al | B | Ca | Mg | Na | Si |
| 001-20 | 98 | 85 | 84 | 87 | 104 | 87 |
| 002-20 | 114 | 97 | 97 | 98 | 122 | 101 |
| Average (20 mg) | 105 ± 3 | 91 ± 3 | 90 ± 2 | 92 ± 2 | 113 ± 4 | 94 ± 3 |
| 003-10 | 116 | 97 | 97 | 102 | 121 | 107 |
| 004-5 | 107 | 97 | 92 | 85 | 122 | 114 |
| 005-5 | 98 | 90 | 86 | 85 | 113 | 104 |
| 006-5 | 93 | 81 | 84 | 84 | 98 | 92 |
| Average (5 mg) | 99 ± 7 | 89 ± 8 | 86 ± 6 | 85 ± 1 | 111 ± 12 | 103 ± 11 |

TABLE 6

Percent Recovery of Insulation from Sample 007, Prepared by Filtration and Ashing

| Insulation Type | Average Percent Recovery (%) | | | | | |
|---|---|---|---|---|---|---|
| | Al | B | Ca | Mg | Na | Si |
| NUKON | 121 | 96 | 94 | 96 | 111 | 96 |
| Isover | 119 | 95 | 93 | 94 | 110 | 95 |
| Walnut Shell | — | — | 94 | 96 | 111 | — |

3. Conclusions

A sample preparation method was developed to prepare strainer insulation samples consisting of 5 to 20 mg of strainer insulation (NUKON and Isover) and walnut shell in approximately 500 mL water.

It was demonstrated that the ICP-AES may successfully analyze the elemental composition of the insulations and walnut shell even at low concentrations (5 mg in 500 mL RO water).

It was also demonstrated that the insulation fibres and walnut shell could be successfully isolated by filtration using ashless filters. The interference of the filter paper was then removed by ashing the sample. The ICP-AES was successful in analyzing the concentration of the insulation present in samples containing as low as 5 mg of insulation. Percent recoveries for each element of each sample were all above 84%.

Appendix B

Strainer Insulation Water Sample Analysis by Inductively Coupled Plasma—Atomic Emission Spectrometry (ICP-AES)

1. Introduction

In the testing of strainers, high volumes of water are passed through containing insulation, walnut shell and/or paint chips to simulate typical reactor debris. Samples are collected down stream of the strainer to investigate passable particulate through the strainer. A method was developed for analyzing the strainer insulation in water samples, to quantify the amount of insulation fibres passing through the strainer. The strainer insulation water samples may consist of insulation (NUKON, Isover or Telisol) and walnut shell or paint chips in 500 mL of water.

To successfully analyze the samples, a sample preparation method was developed for the isolation and digestion of the insulation and walnut shell. This method involved the filtering of samples ashing in a platinum crucible, acid digestion and analysis by Inductively Couple Plasma—Atomic Emission Spectrometry (ICP-AES), using a Perkin-Elmer Optima 3300RL™.

2. Completion of Method Development

The following experiments were performed to complete the development of the sample preparation method to analyze the strainer insulation present in the water samples.

2.1 Determination of Elemental Composition

New supplies of insulation were provided for the completion of the method development to ensure properly aged insulation samples were being used. The elemental composition of each type of insulation (NUKON and Telisol) and walnut shell was determined by ICP-AES. Samples were performed in duplicate to ensure reproducibility of the analysis.

To prepare the insulation samples, approximately 200 mg of each type of insulation was weighed out and placed in 50 mL centrifuge tubes. 10 mL of Aqua Regia was added to each centrifuge tube and left to sit overnight. The following day, 500 mL of hydrofluoric acid was added to each sample. After the addition of acid, residual sample was observed. The samples were then centrifuged and the supernatant siphoned off. The residual was dissolved in 1.5 mL of hydrofluoric acid and recombined with the supernatant. The resulting solution was diluted to 50 mL with Reverse Osmosis (RO) water and analyzed by ICP-AES.

For the walnut shell, 5 mL of RO water and 5 mL of concentrated nitric acid was added to approximately 50 mg of walnut shell in a 50 mL centrifuge tube. The sample was heated, allowed to cool and then centrifuged. As observed in the insulation samples, a residue remained. The supernatant was siphoned off 200 and μL of hydrofluoric acid was added to dissolve the residue. The hydrofluoric acid was recombined with the supernatant and the resulting solution was diluted to 50 mL with RO water. The sample was then analyzed by ICP-AES.

The elemental composition for the insulations and walnut shell are given in Table 1. No significant differences were observed to batch 1 of walnut shell and NUKON analyzed in Appendix A.

TABLE 1

Elemental Composition of Insulations and Walnut Shell

| Material | Al wt % | B wt % | Ca wt % | Mg wt % | Na wt % | Si wt % |
|---|---|---|---|---|---|---|
| Walnut Shell (Batch 2) | <DL* | <DL* | 0.15 ± 0.02 | 0.019 ± 0.002 | 0.003 ± 0.001 | <DL* |
| Walnut Shell (Batch 2) duplicate | <DL* | <DL* | 0.17 ± 0.02 | 0.020 ± 0.002 | 0.009 ± 0.002 | <DL* |
| Average | <DL* | <DL* | 0.16 ± 0.01 | 0.020 ± 0.001 | 0.006 ± 0.004 | <DL* |
| NUKON (Batch 2) | 1.5 ± 0.2 | 1.5 ± 0.2 | 5.4 ± 0.5 | 1.7 ± 0.2 | 11 ± 1 | 25 ± 3 |
| NUKON (Batch 2) duplicate | 1.5 ± 0.2 | 1.5 ± 0.2 | 5.4 ± 0.5 | 1.7 ± 0.2 | 11 ± 1 | 25 ± 3 |
| Average | 1.5 ± 0.2 | 1.5 ± 0.2 | 5.4 ± 0.5 | 1.7 ± 0.2 | 11 ± 1 | 25 ± 3 |
| Telisol (Batch 1) | 0.84 ± 0.09 | 1.9 ± 0.2 | 5.1 ± 0.5 | 1.6 ± 0.2 | 11 ± 1 | 26 ± 3 |
| Telisol (Batch 1) duplicate | 0.86 ± 0.09 | 1.9 ± 0.2 | 5.1 ± 0.5 | 1.6 ± 0.2 | 12 ± 1 | 26 ± 3 |
| Average | 0.85 ± 0.09 | 1.9 ± 0.2 | 5.1 ± 0.5 | 1.6 ± 0.2 | 11 ± 1 | 26 ± 3 |
| Average Insulation Composition** | 1.2 ± 0.1 | 1.7 ± 0.2 | 5.3 ± 0.5 | 1.7 ± 0.2 | 11 ± 1 | 26 ± 3 |

*DL Detection Limit.
**Average of NUKON and Telisol 2.2 Testing of Alumina Crucible A method to analyze the strainer insulation water samples was developed with the use of a platinum crucible for the ashing. This project will require the analysis of several samples at one time, thus the need of more than one crucible was identified. Platinum crucibles are costly and an alternative would have cost benefits. The use of alumina crucibles for the ashing was investigated.

Nine samples were prepared in 600 mL beakers, as summarized in Table 2. Varying weights of NUKON were used to compared the results obtained using a platinum crucible to an alumina crucible, as well as to determine if less than 5 mg of insulation in 500 mL of water may be detected. Four samples containing all three components were prepared to investigate any potential interferences and to ensure reproducibility of the sample preparation method.

Sample weights, as outlined in Table 2, were added to 500 mL of RO water in 600 mL beakers. Samples were stirred for at least 15 minutes (or until uniformly suspended throughout the solution) with a magnetic stirrer.

TABLE 2

Samples Prepared for Alumina Crucible Testing

| | Volume of Water | Weight of Material (mg) | | |
|---|---|---|---|---|
| Sample | (mL) | NUKON | Telisol | Walnut Shell |
| 0 | 500 | 0 | 0 | 0 |
| 1 | 500 | 20.4 | 0 | 0 |
| 2 | 500 | 2.5 | 0 | 0 |
| 3 | 500 | 2.2 | 0 | 0 |
| 4 | 500 | 2.5 | 0 | 0 |
| 5 | 500 | 5.5 | 5.0 | 5.0 |

TABLE 2-continued

Samples Prepared for Alumina Crucible Testing

| | Volume of Water | Weight of Material (mg) | | |
|---|---|---|---|---|
| Sample | (mL) | NUKON | Telisol | Walnut Shell |
| 6 | 500 | 5.3 | 5.1 | 4.9 |
| 7 | 500 | 4.7 | 5.1 | 4.9 |
| 8 | 500 | 2.0 | 2.4 | 2.2 |

To filter the samples, Whatman 40™ ashless cellulose filters were cut to 47 mm in diameter to fit the vacuum filtration apparatus. Samples were filtered using a vacuum filtration set-up. Samples were first passed through the filter paper followed by RO water rinses of the 600 mL beaker to ensure a quantitative transfer of the sample. The filters were then placed in a dessicator until ready to ash.

To ash the samples, each filter paper was transferred to an alumina crucible (with lid). The samples were ashed at 600° C. for 30 minutes. The crucibles were removed from the oven and allowed to cool in a dessicator for approximately 5 minutes. The crucibles were then rinsed into centrifuge tubes using RO water.

For ICP-DES analysis, the samples were evaporated at 115° C. to near dryness and 2 mL of Aqua Regia was added to each sample. The samples were heated to 50° C. for an hour and then to 65° C. for an additional hour. Then 50 mL of hydrofluoric acid was added to each sample and cooled overnight. Once cooled, 10 mL of RO water was added to each sample, shaken and centrifuged. The centrifuged samples were then diluted with an additional 10 mL of RO water before analysis by ICP-AES (Table 3).

TABLE 3

ICP-AES Analysis Results for Alumina Crucible Testing

| Sample | Al (wt %) | B (wt %) | Ca (wt %) | Mg (wt %) | Na (wt %) | Si (wt %) |
|---|---|---|---|---|---|---|
| QA114705 Sample 1 | 1.4 ± 0.1 | 1.4 ± 0.2 | 4.9 ± 0.5 | 1.5 ± 0.2 | 10 ± 1 | 24 ± 2 |
| QA114706 Sample 2 | 0.4 ± 0.1 | 0.47 ± 0.06 | 1.5 ± 0.3 | 0.43 ± 0.05 | 3.3 ± 0.3 | 10 ± 2 |
| QA114707 Sample 3 | 0.4 ± 0.1 | 0.48 ± 0.06 | 1.6 ± 0.3 | 0.43 ± 0.05 | 3.8 ± 0.4 | 10 ± 2 |
| QA114708 Sample 4 | ±0.16 | 0.05 ± 0.03 | ±0.3 | 0.05 ± 0.01 | 0.31 ± 0.07 | 2 ± 2 |
| QA114709 Sample 5 | 0.47 ± 0.05 | 0.69 ± 0.07 | 2.1 ± 0.2 | 0.63 ± 0.06 | 4.6 ± 0.5 | 10 ± 1 |
| QA114710 Sample 6 | 0.72 ± 0.08 | 1.1 ± 0.1 | 3.3 ± 0.3 | 1.1 ± 0.1 | 7.1 ± 0.7 | 16 ± 2 |
| QA114711 Sample 7 | 0.70 ± 0.07 | 1.0 ± 0.1 | 3.1 ± 0.3 | 1.0 ± 0.1 | 6.8 ± 0.7 | 16 ± 2 |
| QA114712 Sample 8 | 0.74 ± 0.09 | 1.1 ± 0.1 | 3.2 ± 0.3 | 1.0 ± 0.1 | 7.1 ± 0.7 | 17 ± 2 |

The percent recoveries achieved by this sample preparation method are given in Table 4. Recoveries for samples 2-4 are extremely low. These samples contain 2.2-2.5 mg of NUKON insulation. This amount of insulation is too low for the detection of this analysis method, thus the detection limit of 5 mg of insulation established in Appendix A remains. All other percent recoveries are greater than 88%. All values have been corrected for the blank and it is assumed that the walnut shell completely ashes (any trace amounts of Ca, Mg, or Na left from the walnut shell is assumed to have a negligible effect on the overall results based on its composition in Table 1).

Table 5 shows a comparison between the testing performed with platinum and alumina crucibles for NUKON. Statistically, there are no differences observed between the results.

TABLE 4

Percent Recoveries for Alumina Crucible Testing

| | Percent Recovery (%) | | | | | |
|---|---|---|---|---|---|---|
| Sample | Al | B | Ca | Mg | Na | Si |
| QA114705 Sample 1 | 92 | 94 | 91 | 88 | 91 | 96 |
| QA114706 Sample 2 | 26 | 31 | 28 | 25 | 30 | 40 |
| QA114707 Sample 3 | 29 | 32 | 30 | 25 | 35 | 40 |
| QA114708 Sample 4 | 0 | 3 | 0 | 3 | 3 | 10 |
| QA114709 Sample 5 | 100 | 101 | 100 | 95 | 105 | 102 |
| QA114710 Sample 6 | 90 | 93 | 92 | 95 | 95 | 93 |
| QA114711 Sample 7 | 89 | 92 | 89 | 93 | 93 | 92 |
| QA114712 Sample 8 | 94 | 94 | 91 | 90 | 97 | 97 |

TABLE 5

Comparison of Platinum and Alumina Crucible Testing

| Sample | Al (wt %) | B (wt %) | Ca (wt %) | Mg (wt %) | Na (wt %) | Si (wt %) |
|---|---|---|---|---|---|---|
| Platinum crucible* | | | | | | |
| NUKON 20 mg Alumina crucible | 1.5 ± 0.1 | 1.4 ± 0.1 | 4.9 ± 0.3 | 1.5 ± 0.1 | 10.4 ± 0.7 | 23 ± 1 |
| NUKON 20 mg | 1.4 ± 0.1 | 1.4 ± 0.2 | 4.9 ± 0.5 | 1.5 ± 0.2 | 10 ± 1 | 24 ± 2 |

*Analysis per formed in [I]

2.3 Analysis of Blind Samples

Fifteen filtered samples were received for analysis. As performed in Section 2.2, the samples were ashed in alumina crucibles (with lid). The samples were ashed in batches of 4 at 600° C. for 30 minutes. They were transferred to centrifuge tubes using an RO water rinse. The samples were then evaporated on a hot block at 115° C. to near dryness. Once evaporated, 2 mL of Aqua Regia was added to each sample. The samples were digested using a hot block at 50° C. for one hour and then at 65° C. for an additional hour. Then 50 mL of hydrofluoric acid was added to each sample and they were allowed to cool overnight. Samples were then diluted to 10 mL with RO water, shaken and centrifuged. The centrifuged samples were then diluted with an additional 10 mL of RO water before being analyzed by ICP-AES. For sample QA116429, a brown residue remained after centrifugation; only the supernatant was analyzed. The results for all samples are given in Table 6.

The results have been corrected for the dilution factor (last 10 mL RO water addition).

TABLE 6

ICP-AES Analysis of Blind Strainer Insulation Filtered Samples

| Sample | Al (mg/L) | B (mg/L) | Ca (mg/L) | Mg (mg/L) | Na (mg/L) | Si (mg/L) |
|---|---|---|---|---|---|---|
| QA116417 R&D Control 001 | 1.8 ± 0.3 | 1.61 ± 0.19 | 16.6 ± 1.7 | 3.2 ± 0.3 | 12 ± 1.2 | 25 ± 3 |
| QA116418 R&D Control 002 | 9.4 ± 1 | 18.3 ± 1.8 | 109 ± 11 | 22 ± 2 | 112 ± 11 | 250 ± 30 |
| QA116419 R&D Control 003 | 12.3 ± 1.3 | 11.2 ± 1.1 | 116 ± 12 | 19.7 ± 2 | 84 ± 8 | 180 ± 18 |
| QA116420 R&D Control 004 | 2.7 ± 0.4 | 3.3 ± 0.3 | 20 ± 2 | 4.1 ± 0.4 | 20 ± 2 | 43 ± 5 |
| QA116421 R&D Control 005 | 3.6 ± 0.5 | 7.2 ± 0.7 | 29 ± 3 | 7.7 ± 0.8 | 45 ± 5 | 98 ± 10 |
| QA116422 R&D Control 006 | 7.2 ± 0.8 | 12.5 ± 1.3 | 48 ± 5 | 13.3 ± 1.3 | 80 ± 8 | 178 ± 18 |

TABLE 6-continued

ICP-AES Analysis of Blind Strainer Insulation Filtered Samples

| Sample | Al (mg/L) | B (mg/L) | Ca (mg/L) | Mg (mg/L) | Na (mg/L) | Si (mg/L) |
|---|---|---|---|---|---|---|
| QA116423 R&D Control 007 | 8.1 ± 0.9 | 8 ± 0.8 | 43 ± 4 | 11.2 ± 1.1 | 61 ± 6 | 129 ± 13 |
| QA116424 R&D Control 008 | ±0.4 | ±0.1 | ±3.0 | ±0.04 | 0.5 ± 0.2 | 1.2 ± 0.6 |
| QA116425 R&D Control 009 | 7.9 ± 0.8 | 9.7 ± 1 | 70 ± 7 | 14.8 ± 1.5 | 71 ± 7 | 153 ± 16 |
| QA116426 R&D Control 010 | 9.8 ± 1.1 | 14.5 ± 1.5 | 100 ± 10 | 19.2 ± 1.9 | 91 ± 9 | 200 ± 20 |
| QA116427 R&D Control 011 | 7.1 ± 0.8 | 12.3 ± 1.2 | 93 ± 9 | 17.4 ± 1.7 | 79 ± 8 | 176 ± 18 |
| QA116428 R&D Control 012 | 11.4 ± 1.2 | 11.8 ± 1.2 | 96 ± 10 | 19.4 ± 1.9 | 84 ± 8 | 183 ± 19 |
| QA116429 R&D Control 013 | 17.6 ± 1.8 | 16.6 ± 1.7 | 119 ± 12 | 26 ± 3 | 129 ± 13 | 270 ± 30 |
| QA116430 R&D Control 014 | 5.6 ± 0.7 | 5.5 ± 0.6 | 35 ± 4 | 8 ± 0.8 | 41 ± 4 | 88 ± 9 |
| QA116431 R&D Control 015 | 9.5 ± 1 | 15.8 ± 1.6 | 60 ± 6 | 17.3 ± 1.7 | 102 ± 10 | 220 ± 20 |

3. Conclusions

A sample preparation method was developed, with the use of alumina crucibles, for the analysis of strainer insulation water samples containing insulation and walnut shell in approximately 500 mL water. It was demonstrated that the ICP-AES may successfully analyze the samples with a detection limit of 5 mg of insulation in 500 mL RO water. The percent recoveries for each element of each test sample were all above 88%.

The blind samples were analyzed using the method described above:
- samples are ashed in an alumina crucible at 600° C. for 30 minutes;
- then transferred to centrifuge tubes using an RO water rinse;
- then evaporated on a hot block at 115° C. to near dryness;
- once evaporated, 2 mL of Aqua Regia is added to each sample;
- the samples are digested using a hot block at 50° C. for one hour, then at 65° C. for an additional hour;
- then 50 mL of hydrofluoric acid is added to each sample and allowed to cool overnight;
- the samples are then diluted to 10 mL with RO water, shaken and centrifuged; and
- an additional 10 mL of RO water is added and the samples are analyzed by ICP-AES.

Appendix C

The Second Batch of ICP-AES Analyses of Fibreglass Samples

1. Fibreglass Samples Prepared for Analyses

A total of 27 samples were prepared. For each sample, a small amount of fibreglass was separated from a bag of aged fibreglass (baked at 300° C. for duration of 24 hours) using tweezers. The fibre was weighed and its mass was recorded. This fibreglass was then added into a 500 ml jar, and the jar was filled to about 500 ml with distilled water and shaken vigorously for 60 seconds. The mixture was then filtered through a 3 micron filter paper. The finished filter paper was dried in a vacuum desiccator to remove moisture. The weight of the fibreglass on the filter paper was also measured and recorded. The sample was placed in a small container (tin) and was sent to ACB for chemical digestion and ICP-AES analyses. The information of the prepared fibreglass samples is listed in Table 1.

TABLE 1

Information of Prepared Fibre Samples

| | Before Filtration | | After Filtration | Filtration |
|---|---|---|---|---|
| Sample # | Nukon (mg) | Telisol (mg) | Fibre (mg) | Recovery (%) |
| 1 | 2.07 | 0 | 1.90 | 91.6 |
| 2 | 4.07 | 0 | 3.73 | 91.6 |
| 3 | 0 | 1.03 | 0.95 | 92.7 |
| 4 | 2.00 | 0 | 1.82 | 91.2 |
| 5 | 1.10 | 0 | 1.02 | 92.4 |
| 6 | 4.24 | 0 | 3.89 | 91.7 |
| 7 | 3.03 | 0 | 2.81 | 92.6 |
| 8 | 0 | 0 | 0 | / |
| 9 | 0 | 3.03 | 2.80 | 92.4 |
| 10* | 0 | 4.17 | 0 | / |
| 11 | 0 | 1.97 | 1.80 | 91.2 |
| 12 | 0 | 0 | 0 | / |
| 13 | 0 | 2.00 | 1.82 | 91.2 |
| 14 | 2.93 | 0 | 2.73 | 93.0 |
| 15 | 4.06 | 0 | 3.71 | 91.4 |
| 16 | 0 | 4.03 | 3.70 | 91.8 |
| 17 | 0 | 2.92 | 2.70 | 92.5 |
| 18 | 0 | 0.96 | 0.89 | 93.2 |
| 19 | 0 | 0 | 0 | / |
| 20 | 1.07 | 0 | 0.99 | 92.5 |
| 21 | 2.87 | 0 | 2.67 | 93.2 |
| 22 | 1.84 | 0 | 1.68 | 91.2 |
| 23 | 0 | 4.36 | 3.98 | 91.3 |
| 24 | 0 | 1.02 | 0.95 | 93.1 |
| 25 | 0 | 2.95 | 2.73 | 92.5 |
| 26 | 1.00 | 0 | 0.93 | 93.0 |
| 27 | 0 | 2.03 | 1.87 | 92.1 |

2. ICP-AES Analyses Results

For each sample, the filter paper was transferred from the tin to an alumina crucible. The sample was then ashed at 600° C. for 30 minutes in an oven. The ashed sample was digested by Aqua Regia and hydrofluoric acid. The sample was then diluted to 10 mL by adding distilled water and analyzed by ICP-AES. The elemental concentration results are provided in Table 2.

TABLE 2

Sample Elemental Concentration from ICP-AES Analyses

| Sample # | Al (mg/L) | B (mg/L) | Ca (mg/L) | Mg (mg/L) | Na (mg/L) | Si (mg/L) |
|---|---|---|---|---|---|---|
| 1 | 16.1 ± 1.6 | 3.2 ± 0.4 | 12.6 ± 1.3 | 4 ± 0.4 | 41 ± 4 | 49 ± 5 |
| 2 | 5.4 ± 0.6 | 4.8 ± 0.5 | 18 ± 1.9 | 5.7 ± 0.6 | 41 ± 4 | 74 ± 8 |

TABLE 2-continued

Sample Elemental Concentration from ICP-AES Analyses

| Sample # | Al (mg/L) | B (mg/L) | Ca (mg/L) | Mg (mg/L) | Na (mg/L) | Si (mg/L) |
|---|---|---|---|---|---|---|
| 3 | <0.4 | <0.17 | 0.99 ± 0.13 | 0.4 ± 0.05 | 4.8 ± 0.8 | 2.7 ± 1.8 |
| 4 | 5.7 ± 0.6 | 1.9 ± 0.2 | 8.3 ± 0.8 | 5.4 ± 0.5 | 21 ± 2 | 30 ± 4 |
| 5 | 2.2 ± 0.4 | 1.9 ± 0.2 | 7.6 ± 0.8 | 2.5 ± 0.3 | 17 ± 1.9 | 29 ± 4 |
| 6 | 3.2 ± 0.5 | 3.1 ± 0.4 | 10.9 ± 1.2 | 3.8 ± 0.4 | 26 ± 3 | 47 ± 6 |
| 7 | 3.7 ± 0.5 | 3.6 ± 0.4 | 12.4 ± 1.2 | 4.1 ± 0.4 | 29 ± 3 | 56 ± 6 |
| 8 | <0.4 | <0.17 | 0.74 ± 0.12 | 5.4 ± 0.5 | 2.4 ± 0.6 | <2.5 |
| 9 | 2.5 ± 0.4 | 4.5 ± 0.5 | 12.5 ± 1.3 | 4.6 ± 0.5 | 29 ± 3 | 59 ± 6 |
| 10 | 1.2 ± 0.3 | 2 ± 0.3 | 5.6 ± 0.6 | 2.2 ± 0.2 | 13.9 ± 1.6 | 26 ± 3 |
| 11 | 1 ± 0.3 | 1.4 ± 0.2 | 4.6 ± 0.5 | 1.7 ± 0.17 | 10.4 ± 1.2 | 20 ± 3 |
| 12 | 0.5 ± 0.3 | <0.17 | 0.63 ± 0.11 | 2.9 ± 0.3 | 1.3 ± 0.6 | <2.5 |
| 13 | 1.2 ± 0.3 | 2.2 ± 0.3 | 6.4 ± 0.7 | 2.4 ± 0.2 | 14.6 ± 1.6 | 29 ± 4 |
| 14 | 2.5 ± 0.4 | 2.3 ± 0.3 | 8.5 ± 0.9 | 2.7 ± 0.3 | 19 ± 2 | 36 ± 4 |
| 15 | 3.3 ± 0.5 | 3.1 ± 0.4 | 11.1 ± 1.2 | 3.5 ± 0.3 | 25 ± 3 | 47 ± 5 |
| 16 | 3.5 ± 0.4 | 6.6 ± 0.7 | 17.8 ± 1.8 | 7.4 ± 0.7 | 41 ± 4 | 87 ± 9 |
| 17 | 1.3 ± 0.3 | 2.5 ± 0.3 | 8 ± 0.8 | 3 ± 0.3 | 16.5 ± 1.8 | 34 ± 4 |
| 18 | 0.5 ± 0.3 | 0.53 ± 0.14 | 1.9 ± 0.2 | 1.1 ± 0.11 | 4.4 ± 0.7 | 8 ± 2 |
| 19 | <0.4 | <0.17 | 0.99 ± 0.12 | 0.73 ± 0.08 | 1 ± 0.6 | <2.5 |
| 20 | 0.6 ± 0.3 | 0.29 ± 0.12 | 1.84 ± 0.2 | 2.4 ± 0.2 | 3.2 ± 0.7 | 5 ± 1.8 |
| 21 | 2 ± 0.3 | 1.9 ± 0.2 | 7.2 ± 0.8 | 2.7 ± 0.3 | 14.7 ± 1.6 | 29 ± 4 |
| 22 | 2.2 ± 0.4 | 1.9 ± 0.2 | 7 ± 0.7 | 2.4 ± 0.2 | 15.7 ± 1.7 | 30 ± 4 |
| 23 | 4.3 ± 0.5 | 8.5 ± 0.9 | 23 ± 2 | 8.4 ± 0.8 | 52 ± 5 | 111 ± 11 |
| 24 | 0.8 ± 0.3 | 0.86 ± 0.16 | 3.1 ± 0.3 | 2.7 ± 0.3 | 6.3 ± 0.9 | 13 ± 2 |
| 25 | 2.7 ± 0.4 | 5.5 ± 0.6 | 14.8 ± 1.5 | 6.1 ± 0.6 | 35 ± 4 | 73 ± 8 |
| 26 | 0.6 ± 0.3 | 0.43 ± 0.13 | 2.1 ± 0.3 | 1.31 ± 0.13 | 4.2 ± 0.7 | 7.7 ± 1.9 |
| 27 | 1.3 ± 0.3 | 2.1 ± 0.3 | 6.7 ± 0.7 | 2.9 ± 0.3 | 14.3 ± 1.6 | 29 ± 4 |

3. Fibre Amount Determination

The amount of fibreglass on each filter paper may be determined from the elemental concentration results as listed in Table 2. The calculation is demonstrated in the below equation:

$$\text{Fibre mass} = \frac{\text{element mass}}{\text{elemental compositon}}, \quad (1)$$

where, element mass is equal to elemental concentration times sample volume (10 mL), and elemental composition is listed in Table 1 of Appendix B.

The fibreglass amount determined by the use of equation (1) for each sample is listed in Table 3 along with the actual fibre amount.

TABLE 3

Fibre Amount Determined by Elemental Composition

| Sample # | Actual fibre amount (mg) | Fibre amount by Al (mg) | Fibre amount by B (mg) | Fibre amount by Ca (mg) | Fibre amount by Mg (mg) | Fibre amount by Na (mg) | Fibre amount by Si (mg) |
|---|---|---|---|---|---|---|---|
| 1 | 2.07 | 10.7 | 2.1 | 2.3 | 2.4 | 3.7 | 2.0 |
| 2 | 4.07 | 3.6 | 3.2 | 3.3 | 3.4 | 3.7 | 3.0 |
| 3 | 1.03 | 0.3 | 0.1 | 0.2 | 0.2 | 0.4 | 0.1 |
| 4 | 2.00 | 3.8 | 1.3 | 1.5 | 3.2 | 1.9 | 1.2 |
| 5 | 1.10 | 1.5 | 1.3 | 1.4 | 1.5 | 1.5 | 1.2 |
| 6 | 4.24 | 2.1 | 2.1 | 2.0 | 2.2 | 2.4 | 1.9 |
| 7 | 3.03 | 2.5 | 2.4 | 2.3 | 2.4 | 2.6 | 2.2 |
| 8 | 0 | 0 | 0 | 0.1 | 3.2 | 0.2 | 0 |
| 9 | 3.03 | 2.9 | 2.4 | 2.5 | 2.9 | 2.6 | 2.3 |
| 10 | / | / | / | / | / | / | / |
| 11 | 1.97 | 1.2 | 0.7 | 0.9 | 1.1 | 0.9 | 0.8 |
| 12 | 0 | 0.3 | 0 | 0.1 | 1.7 | 0.1 | 0 |
| 13 | 2 | 1.4 | 1.2 | 1.3 | 1.5 | 1.3 | 1.1 |
| 14 | 2.93 | 1.7 | 1.5 | 1.6 | 1.6 | 1.7 | 1.4 |
| 15 | 4.06 | 2.2 | 2.1 | 2.1 | 2.1 | 2.3 | 1.9 |
| 16 | 4.03 | 4.1 | 3.5 | 3.5 | 4.6 | 3.7 | 3.3 |
| 17 | 2.92 | 1.5 | 1.3 | 1.6 | 1.9 | 1.5 | 1.3 |
| 18 | 0.96 | 0.6 | 0.3 | 0.4 | 0.7 | 0.4 | 0.3 |
| 19 | 0 | 0 | 0 | 0.2 | 0.4 | 0.1 | 0 |
| 20 | 1.07 | 0.4 | 0.2 | 0.3 | 1.4 | 0.3 | 0.2 |
| 21 | 2.87 | 1.3 | 1.3 | 1.3 | 1.6 | 1.3 | 1.2 |
| 22 | 1.84 | 1.5 | 1.3 | 1.3 | 1.4 | 1.4 | 1.2 |
| 23 | 4.36 | 5.1 | 4.5 | 4.5 | 5.3 | 4.7 | 4.3 |
| 24 | 1.02 | 0.9 | 0.5 | 0.6 | 1.7 | 0.6 | 0.5 |
| 25 | 2.95 | 3.2 | 2.9 | 2.9 | 3.8 | 3.2 | 2.8 |
| 26 | 1.00 | 0.4 | 0.3 | 0.4 | 0.8 | 0.4 | 0.3 |
| 27 | 2.03 | 1.5 | 1.1 | 1.3 | 1.8 | 1.3 | 1.1 |

As reported in Appendix B, for Nukon and Telisol fibreglass, elemental compositions of B, Ca, Mg, Na and Si are very similar. Thus, it is difficult to use those elements to distinguish Nukon from Telisol. But the Al composition of Nukon is almost double than that of Telisol, thus Al may be used to identify Telisol from Nukon if necessary. In the calculation process of Table 3, it was first assumed that the fibreglass material was Nukon and the fibre amount was determined by the weight percentage of each of the six elements of Nukon, thus six calculated fibre amounts for each sample. If the fibre amount determined by Al is less than the amounts determined by other elements, it is known that the fibre material of that sample should be Telisol. The fibre amount of that sample is then re-calculated by using Telisol elemental composition. This method was effective in identifying samples 9, 11, 13, 16, 17, 18, 23, 24, 25 and 27 as Telisol and their fibre amounts were calculated by using Telisol elemental composition as listed in Table 3. Sample 3 could not be detected as either Nukon or Telisol because its Al concentration as listed in Table 2 is under detection limit of ICP-AES.

Figure 2:
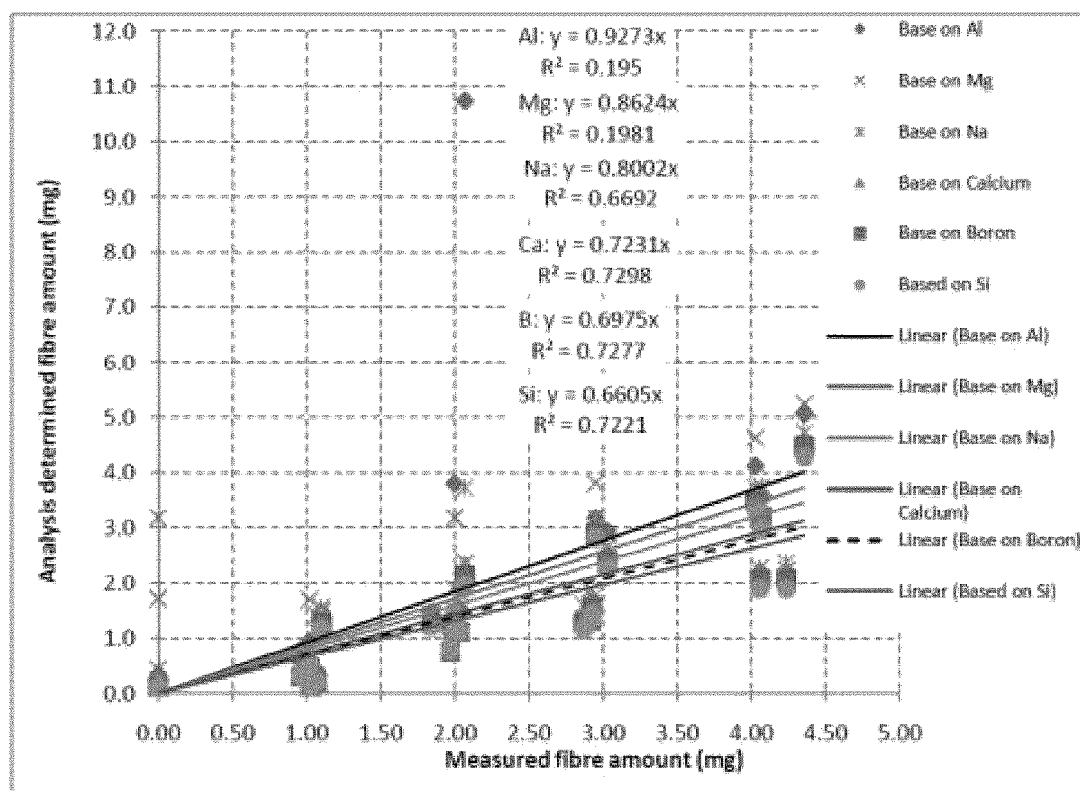
FIG. 2 is a graph showing analysis determined fibre amount by different element.

Actual fibre amounts are plotted against analysis-determined fibre amounts in FIG. 2 (weights in column 2 versus weights in columns 3 to 8 in Table 3 separately). A linear trend line is added to each data series. Trend line equations and its coefficient of determination for each element are provided in FIG. 2. As may be seen from FIG. 2, fibre amounts determined by both Al and Mg have a wide range of scatter, while fibre amounts determined by B and Si are almost coincident with each other with a narrower range of dispersion. Low $R^2$ values for both Al and Mg trend lines indicate that the analysis determined value correlate poorly with the actual fibre amounts. The relatively consistent coefficients of the linear equations and the higher $R^2$ values for elements Na, Ca, B and Si indicate that these elements could be used to determine the fibre amount in each sample. The reason for the widely scattered data from elements Al and Mg was possibly due to contamination of the sample material. Liner regression equations for Na, B, Ca and Si all have approximately the same slope of 0.7, which indicate that the chemical digestion process may reliably recover 70% of the elements on average.

It should be noted that since both Nukon and Telisol contain 25% (weight) of Si, Si has a relatively high tolerance for contamination. For this reason, it is advisable to use elements that have high percentage weight (wt %) in the fibreglass material to determine fibre mass. Since both fibre materials contain around 11% of sodium, an alternative way is to average the fibre mass determined by both Na and Si to diminish the effects of the scattered data points.

The range of dispersion of the fibre mass determined by each element was investigated by looking at the coefficient of determination ($R^2$) of the linear regression equation of the data set. The linear regression equation and it $R^2$ value for each element are provided in FIG. 2. The much lower $R^2$ value (around 0.19) from elements Al and Mg indicates that the data sets are more widely dispersed than those of other elements, which have a $R^2$ value of 0.7, and thus ICP-AES data from elements Al and Mg should not be used in the fibre mass calculation.

Figure 3:
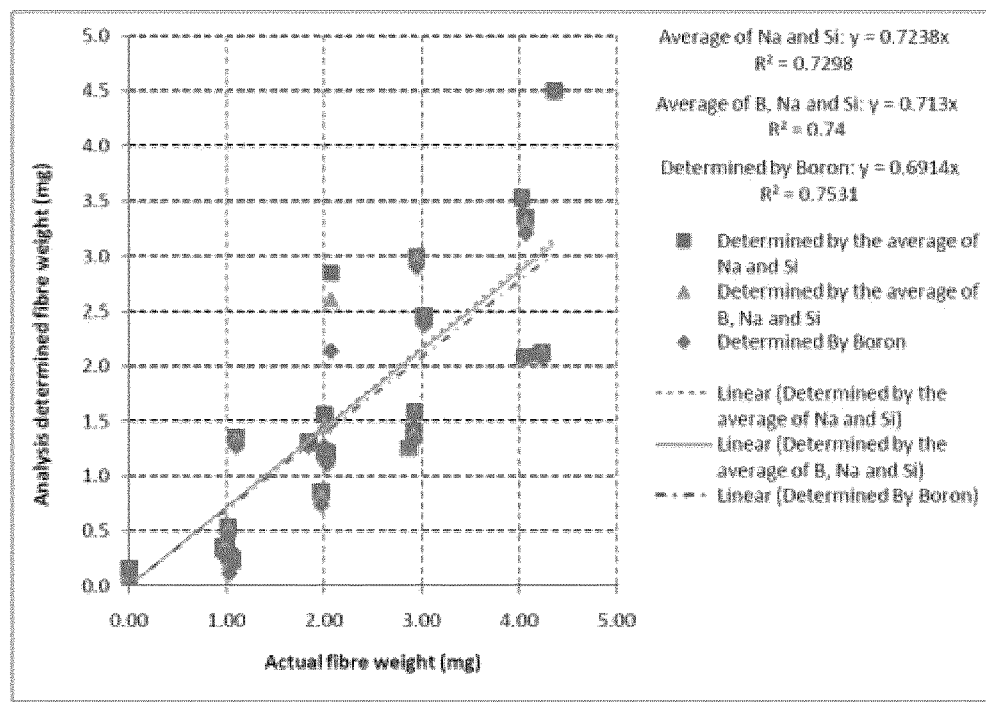
FIG. 3 is a graph showing analysis determined fibre amount by B, Na and Si.

The fibre amount of each sample could also be determined by averaging the results from different elements. The fibre amounts determined by B, by the average of Na and Si and by the average of B, Na and Si are plotted against the actual fibre amount in FIG. 3. From FIG. 3, it may be seen that the fibre amount determined by the average of Na and Si has the best recovery rate among the three methods. The inclusion of test results from boron has neither beneficial nor detrimental effect on the results of averaging both Na and Si. Thus, data from B do not need to be included in the fibre mass calculation, but it may be used to judge whether data from Na and Si are consistent.

4. Fibre Mass Prediction

For fibre mass determination by using chemical digestion and ICP-AES method, it is preferable to take a large water sample to ensure that the fibre content is greater than 5 mg. In case this cannot be achieved, methods have been investigated to obtain a reliable prediction.

If there are enough water samples for analysis, the best-fit prediction may be used. The prediction equation is show below:

$$m_{p1}=1.3 \times m_a+0.15, \quad (2)$$

where:
$m_{p1}$=predicted fibre mass based on best fit; and
$m_a$=analysis determined fibre mass based on the average of Na and Si.

Figure 4:
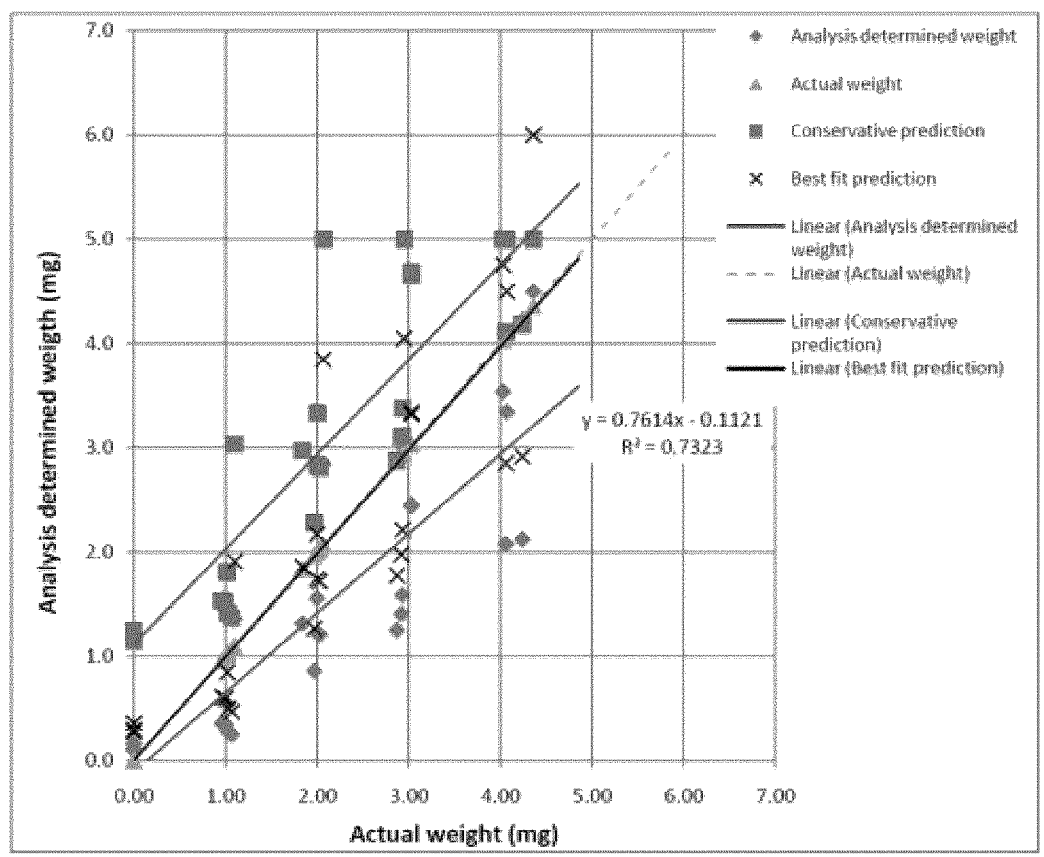
FIG. 4 is a graph showing fibre mass prediction.

Equation (2) is derived from the best fit equation of the analysis determined fibre mass (average of Na and Si) to the actual fibre mass. The equation is shown in FIG. 4 as:

$$y=0.7614x-0.1121.$$

Solving the equation to obtain: $x=1.3y+0.15$.

Note the best fit prediction by using equation (2) has no conservatism built-in. This is shown in FIG. 4 by the 'x' shaped marker. Some predicted data points are above the line y=x (dotted line in FIG. 4), while some are below. But the average is on line y=x as indicated by the coincidence of the central trendline and the dotted line.

If very few samples are available, a conservative prediction method should be used. The objective of this method is to ensure that all the predicted data points are located above line y=x. Equation (3) is used for this purpose:

$$m_{p2}=1.5 \times m_a+1, \quad (3)$$

where:
$m_{p2}$=conservatively predicted fibre mass; and
$m_a$=analysis determined fibre mass based on the average of Na and Si.

The predicted data points by using Equation (3) are plotted in FIG. 4 as square shaped markers. As may be seen from FIG. 4, all the predicted data points are located above line y=x. Note a treatment has been done for predicted data greater than 5 mg in the figure. If Equation (3) predicted data is greater than 5 mg, 5 mg is used as the predicted fibre mass instead.

We claim:

1. A method of quantifying fibre content of a water, particulate and fibre mixture, comprising:
   providing a sample of the water, particulate and fibre mixture;
   filtering the sample of the water, particulate and fibre mixture to produce a particulate and fibre mixture;
   burning the particulate and fibre mixture to produce a fibre sample;
   dissolving the fibre sample to produce a fibre solution;
   analyzing the fibre solution to determine an elemental content of the fibre solution; and
   comparing the elemental content to a known elemental content to estimate the fibre content.

2. The method of claim 1, wherein the step of filtering comprises filtering the sample of the water, particulate and fibre mixture with an ashless filter.

3. The method of claim 2, wherein the step of burning comprises thermally decomposing the particulate of the particulate and fibre mixture.

4. The method of claim 3, wherein the step of burning comprises ashing of the particulate and fibre mixture in an alumina crucible.

5. The method of claim 1, wherein the step of burning comprises thermally decomposing the particulate of the particulate and fibre mixture.

6. The method of claim 5, wherein the step of burning comprises ashing of the particulate and fibre mixture in an alumina crucible.

7. The method of claim 1, wherein the step of dissolving comprises digesting the fibre sample with hydrofluoric acid.

8. The method of claim 1, wherein the step of analyzing comprises using Inductively Coupled Plasma-Atomic Emission Spectrometry (ICP-AES) analysis.

9. The method of claim 1, wherein the elemental content comprises an elemental composition for at least one of B, Ca, Mg, Na and Si.

10. The method of claim 9, wherein the elemental content comprises an elemental composition for each of B, Ca, Mg, Na and Si.

11. The method of claim 1, wherein the elemental content comprises an elemental composition for at least one of Na and Si.

12. The method of claim 11, wherein the elemental content comprises an elemental composition for each of Na and Si.

13. The method of claim 1, wherein the step of comparing comprises determining a fibre weight of the fibre solution.

14. The method of claim 13, wherein the step of comparing comprises determining a weight for each element of the elemental content of the fibre solution, and the fibre weight is determined based on the weight for each element.

15. A method, comprising:
providing a sample of a water, particulate and fibre mixture;
filtering the sample of the water, particulate and fibre mixture to produce a particulate and fibre mixture;
thermally decomposing the particulate in the particulate and fibre mixture to produce a fibre sample;
digesting the fibre sample with an acid to produce a fibre solution;
analyzing the fibre solution to determine an elemental content of the fibre solution; and
comparing the elemental content of the fibre solution to a known elemental content to estimate a fibre content of the sample of the water, particulate and fibre mixture.

16. The method of claim 15, wherein the step of filtering comprises filtering the sample of the water, particulate and fibre mixture with an ashless filter.

17. The method of claim 15, wherein the step of thermally decomposing comprises ashing of the particulate and fibre mixture in an alumina crucible.

18. The method of claim 15, wherein the step of digesting comprises digesting the fibre sample with hydrofluoric acid.

19. The method of claim 15, wherein the step of analyzing comprises using Inductively Coupled Plasma-Atomic Emission Spectrometry (ICP-AES) analysis.

20. A method, comprising:
providing a sample of a water, particulate and fibre mixture;
filtering the sample of the water, particulate and fibre mixture to produce a particulate and fibre mixture;
burning the particulate and fibre mixture to produce a fibre sample;
dissolving the fibre sample to produce a fibre solution;
analyzing the fibre solution to determine an elemental content of the fibre solution;
determining a weight for each element of the elemental content of the fibre solution; and
determining a fibre weight based on the weight for each element.

* * * * *